US012599448B2

(12) United States Patent
Xu et al.

(10) Patent No.: US 12,599,448 B2
(45) Date of Patent: Apr. 14, 2026

(54) OPERATION ENABLING CONTROL SYSTEM AND ROBOT-ASSISTED SURGICAL DEVICE HAVING THE SYSTEM

(71) Applicant: BEIJING SURGERII ROBOTICS COMPANY LIMITED, Beijing (CN)

(72) Inventors: Kai Xu, Beijing (CN); Aolin Tang, Beijing (CN)

(73) Assignee: BEIJING SURGERII ROBOTICS COMPANY LIMITED, Beijing (CN)

( * ) Notice: Subject to any disclaimer, the term of this patent is extended or adjusted under 35 U.S.C. 154(b) by 1330 days.

(21) Appl. No.: 17/417,824

(22) PCT Filed: Dec. 27, 2019

(86) PCT No.: PCT/CN2019/128986
§ 371 (c)(1),
(2) Date: Jun. 24, 2021

(87) PCT Pub. No.: WO2020/135665
PCT Pub. Date: Jul. 2, 2020

(65) Prior Publication Data
US 2022/0054207 A1 Feb. 24, 2022

(30) Foreign Application Priority Data

Dec. 27, 2018 (CN) .......................... 201811610863.5

(51) Int. Cl.
*A61B 34/35* (2016.01)
*A61B 34/00* (2016.01)
(Continued)

(52) U.S. Cl.
CPC .............. *A61B 34/35* (2016.02); *A61B 34/25* (2016.02); *A61B 34/32* (2016.02); *A61B 34/74* (2016.02); *G16H 40/63* (2018.01); *H03K 19/20* (2013.01)

(58) Field of Classification Search
CPC ........ A61G 34/35; A61B 34/25; A61B 34/32; A61B 34/74; G16H 40/63; H03K 19/20
See application file for complete search history.

(56) References Cited

U.S. PATENT DOCUMENTS 6,948,503 B2 * 9/2005 Refior ................ A61B 18/1206
606/34
7,904,206 B2 * 3/2011 Shioda ................... A61B 90/50
700/250
(Continued)

FOREIGN PATENT DOCUMENTS

CN 101926680 A 12/2010
CN 105395254 A 3/2016
(Continued)

OTHER PUBLICATIONS

Office Action in corresponding Japanese Application No. 2021-533727 dated May 10, 2022 (5 pages).
(Continued)

*Primary Examiner* — Crystal L Hammond
*Assistant Examiner* — Samantha L Faubert
(74) *Attorney, Agent, or Firm* — Bayes PLLC

(57) ABSTRACT

An operation enabling control system and a robot-assisted surgical device having the operation enabling control system are disclosed. The operation enabling control system includes a switch element and a logic AND circuit. A first terminal of the switch element is connected with a power supply. A second terminal of the switch element is connected with an automated driving system of a robot-assisted surgical system. The logic AND circuit comprises a first input terminal and a second input terminal. The first input terminal is configured to receive a sensor status of the robot-assisted surgical system. The second input terminal is configured to receive a control signal. An output terminal of the logic
(Continued)

AND circuit is connected with a control terminal of the switch element.

9 Claims, 4 Drawing Sheets

(51) Int. Cl.

| | |
|---|---|
| *A61B 34/32* | (2016.01) |
| *G16H 40/63* | (2018.01) |
| *H03K 19/20* | (2006.01) |

(56) References Cited

U.S. PATENT DOCUMENTS

| | | | | |
|---|---|---|---|---|
| 7,933,676 | B2 | 4/2011 | Schuster | |
| 11,311,345 | B2 * | 4/2022 | Robinson | A61B 34/37 |
| 11,432,885 | B2 * | 9/2022 | Shelton, IV | G16H 20/40 |
| 2011/0144636 | A1 * | 6/2011 | Alexander | A61B 18/00 606/34 |
| 2012/0071892 | A1 | 3/2012 | Itkowitz et al. | |
| 2012/0298719 | A1 | 11/2012 | Shelton, IV et al. | |
| 2014/0324070 | A1 | 10/2014 | Min et al. | |
| 2015/0280424 | A1 | 10/2015 | Leimbach et al. | |
| 2015/0326281 | A1 | 11/2015 | Ma | |
| 2018/0168624 | A1 | 6/2018 | Shelton, IV et al. | |

FOREIGN PATENT DOCUMENTS

| | | | | | |
|---|---|---|---|---|---|
| CN | 107334531 | A | | 11/2017 | |
| CN | 206729972 | U | * | 12/2017 | |
| CN | 109730772 | A | | 5/2019 | |
| EP | 2939633 | A1 | | 4/2015 | |
| JP | 2016146184 | A | | 8/2016 | |
| JP | 2017513558 | A | * | 6/2017 | G05F 5/00 |
| KR | 20140129702 | A | | 11/2014 | |
| WO | 2005017849 | A1 | | 2/2005 | |

OTHER PUBLICATIONS

Supplementary Partial European Search Report in corresponding European Application No. EP19902519 dated Jan. 4, 2022 (11 pages).
Office Action in corresponding European Application No. 19902519.8 dated Mar. 30, 2022 (14 pages).
International Search Report in corresponding PCT Application No. PCT/CN/2019/128986 dated Mar. 26, 2020 (5 pages).
Chinese Office Action from corresponding Chinese Application No. 2018116108635 dated Feb. 18, 2020 (2 pages).
Office Action in related Korean Application No. 10-2021-7023753 dated Jan. 30, 2023 (6 pages).

* cited by examiner

1

OPERATION ENABLING CONTROL SYSTEM AND ROBOT-ASSISTED SURGICAL DEVICE HAVING THE SYSTEM

CROSS-REFERENCE TO RELATED APPLICATIONS

This patent application is a U.S. National Phase of International Application No. PCT/CN2019/128986, filed on Dec. 27, 2019, which claims priority to Chinese Patent Application No. 201811610863.5, filed on Dec. 27, 2018. The entire contents of each of the above-identified applications are incorporated herein by reference.

TECHNICAL FIELD

This application relates to an operation enabling control system and a robot-assisted surgical device equipped with the operation enabling control system, and relates to the technical field of medical device.

BACKGROUND

With advance of automation technology, more and more operations no longer require a surgeon to stand by an operating table to perform. The chief surgeon can sit on a console and control an automation device next to the operating table through remote operation to complete corresponding work. This remote teleoperation manner can reduce work intensity and pressure of surgeons, and greatly improve their work ability and efficiency through assistance of advanced technologies (such as robotics, artificial intelligence technology). This advanced surgical manner also brings risks although bringing advantages. A significant risk is that undesirable actions of remote automated surgical device may occur due to negligence of an operator or malfunction of a software, causing injury to the patient or surgical assistant.

At present, widely used Da Vinci surgical robot in the world uses a detection sensor installed on 3D eyeglass bracket to detect whether the surgeon is operating the device. If the surgeon's head leaves the 3D eyeglass bracket (the sensor cannot detect it), the system will (through software) prohibit the surgeon from controlling the remote automated surgical device. Similar devices in China also use similar designs to prevent accidents. For example, the surgeon console of laparoscopic surgical robot system designed by Suzhou Kangdo Robot Co., Ltd. uses Kinect sensor, opposite-type photoelectric sensor and capacitive sensor installed on operation handle to ensure the safety of the device in use. The Kinect sensor is used to monitor in real time whether the operator's face deviates, to monitor whether the operator's sight is away from the display. The opposite-type photoelectric sensor detects whether the operator's foot leaves pedal device, and the capacitive sensor on the operation handle monitors whether the operator's hand leaves the gripper. The triple mechanisms prevent the occurrence of mis-operation. Existing robot-assisted surgical systems (also referred to as robotic-assisted surgical systems) all use sensors to detect whether the user has an operation intention, so as to prevent unconscious mis-operation from occurring. However, this method cannot prevent mis-operation caused by other single failure (such as software failure). The operator can only press emergency stop switch to try to prevent the unexpected movement of the automated surgical device, but this step requires more response time, and during this time, the hazard may have already occurred.

As shown in FIG. 1, traditional robot-assisted surgical device usually includes two parts: a console and an automated surgical device (the two parts can also be installed together to form one device). The surgeon uses a manipulator on the console to control various automated surgical device to complete the corresponding work. The multi-sensor combination system on the console is used to detect whether the operator is ready for remote operation (usually two or more sensors are used to meet the requirements for single failure detection in the medical device standard, that is, when a component fails, it can be detected, and the failure cannot cause a risk of harm to the user or patient). When all the sensors detect that the operator is in place, the control system sends corresponding software control instructions to the automated driving system to enter electrical driven motion enabled state, so as to respond to the corresponding instructions input by the operator on the console at any time. It can be seen that in the work procedure, the master-slave teleoperation control system is at a core position. Once it fails, the entire automated surgical device is at risk of losing control.

SUMMARY

In view of the above problems, an objective of the present disclosure is to provide an operation enabling control system and a robot-assisted surgical device with the system, which can activate a motion enabled state of the corresponding automated device through two independent control loops of software control and hardware signal.

Thus, the present disclosure discloses the following technical solutions:

In a first aspect, the present disclosure provides an operation enabling control system. The system comprises a control device, a switch element and a logic AND circuit. The control device comprises an input terminal and an output terminal, and the input terminal of the control device is connected with a robot-assisted surgical system to receive an operation instruction. A terminal of the switch element is connected with an external power supply system, and another terminal of the switch element is connected with an automated driving system of the robot-assisted surgical system. The logic AND circuit comprises a first input terminal and a second input terminal. The first input terminal of the logic AND circuit is to receive a sensor status of the robot-assisted surgical system, and the second input terminal of the logic AND circuit is connected with the output terminal of the control device. An output terminal of the logic AND circuit is connected with a control terminal of the switch element. The logic AND circuit performs a logical AND operation on signals received by the first input terminal and the second input terminal, and a result of the operation is output to control on and off of the switch element.

In addition, a feedback circuit for detecting whether the switch element has a supply voltage is further provided between the switch element and the control device.

In addition, the feedback circuit uses a level detection circuit.

in a second aspect, the present disclosure provides a robot-assisted surgical device, including a console and an automated surgical device. The console comprises a multi-sensor combination system, and the multi-sensor combination system is to detect whether an operator is ready for operation. The automated surgical device comprises a surgical device power supply unit, a surgical control unit, an operation enabling control system, and an automated driving system. The operation enabling control system comprises a control device, a switch element, and a logical AND circuit. The operation enabling control system is arranged between the surgical device power supply unit and the automated driving system. An input terminal of the control device is connected with the surgical control unit. A terminal of the switch element is connected with the surgical device power supply unit, and another terminal of the switch element is connected with the automated driving system. A first input terminal of the logic AND circuit is to receive a multi-sensor status, and a second input terminal of the logic AND circuit is connected with an output terminal of the control device. An output terminal of the logic AND circuit is connected with a control terminal of the switch element.

In addition, the first input terminal of the logical AND circuit is connected with each sensor in the multi-sensor combination system.

In addition, the console further comprises another logical AND circuit. An input terminal of the another logical AND circuit is connected with each sensor in the multi-sensor combination system, and an output terminal of the another logic AND circuit is connected with the first input terminal of the logic AND circuit.

In addition, a feedback circuit for detecting whether the switch element has a supply voltage is further provided between the switch element and the control device.

In addition, the console further comprises a console power supply unit, a switch, a button, a manipulator, a console control unit, a display, a microphone, and a speaker. The automated surgical device further comprises a switch, a button, a display, a microphone, a speaker, and a corresponding surgical tool. The console power supply unit is connected with an external power supply network. Input terminals of the console control unit are connected with sensors in the multi-sensor combination system, the switch, the button, the manipulator, and the microphone, respectively, and an output terminal of the console control unit is connected with the corresponding display and speaker to assist the operator to interact with the console. The surgical control unit is connected bidirectionally with the console control unit, the control device, and the automated driving system o perform interactive communication. The surgical control unit controls corresponding electrical driven motion through the automated driving system to drive a surgical tool to move. Input terminals of the surgical control unit are connected with corresponding switch, the button and the microphone, respectively, and an output terminal of the surgical control unit are connected with corresponding display and speaker to assist the operator to interact with the automated driving system.

The present disclosure has the following advantages due to the above technical solutions:

1. the operation enabling control system of the present disclosure is used to take over driving power supply management of the automated surgical device. The driving power supply is changed from original direct power supply to controlled power supply, so that when the system has not entered the enabled state (that is, when the operator is not ready to start control), the driving power supply of the entire automated driving system is completely turned off, and the reliable turnoff of the driving power supply can be ensured through feedback detection;

2. Compared with the traditional robot-assisted surgical system, the robot-assisted surgical device with the operation enabling control system of the present disclosure can turn off the power supply of the automated surgical device more reliably and quickly, so that unexpected mis-operations can be stopped faster. The reliability of system operation can be further improved, the probability of accidental actions that may be caused by system failures can be reduced, and the risk of injury caused by mis-operations of the automated surgical device can be reduced.

In summary, the present disclosure can be widely applied to robot-assisted surgical systems.

DETAILED DESCRIPTION

In order to make objectives, technical solutions, and advantages of embodiments of the present disclosure clear, the technical solutions in the embodiments of the present disclosure will be described clearly and completely with reference to accompanying drawings in the embodiments of the present disclosure. Obviously, a part of, rather than all of, the embodiments of the present disclosure are described. Based on the embodiments of the present disclosure, all other embodiments obtained by one of ordinary skill in the art without inventive work shall fall within the protection scope of the present disclosure.

Embodiment 1

Figure 1:
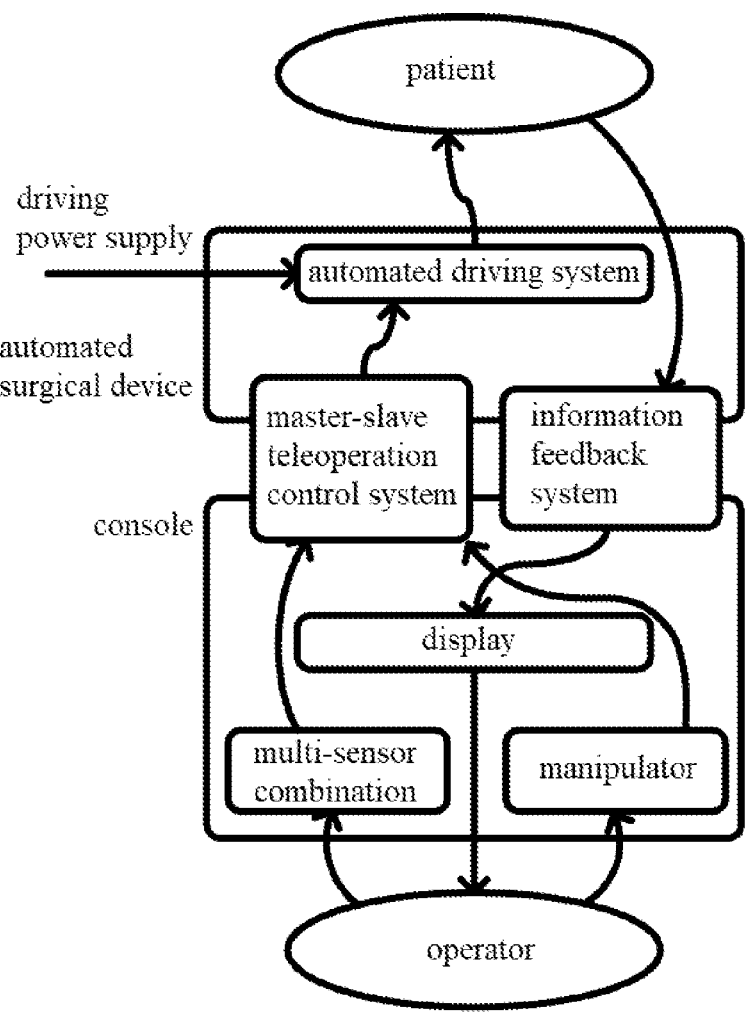
FIG. 1 is a schematic diagram of a workflow of a traditional robot-assisted surgical system.
Figure 2:
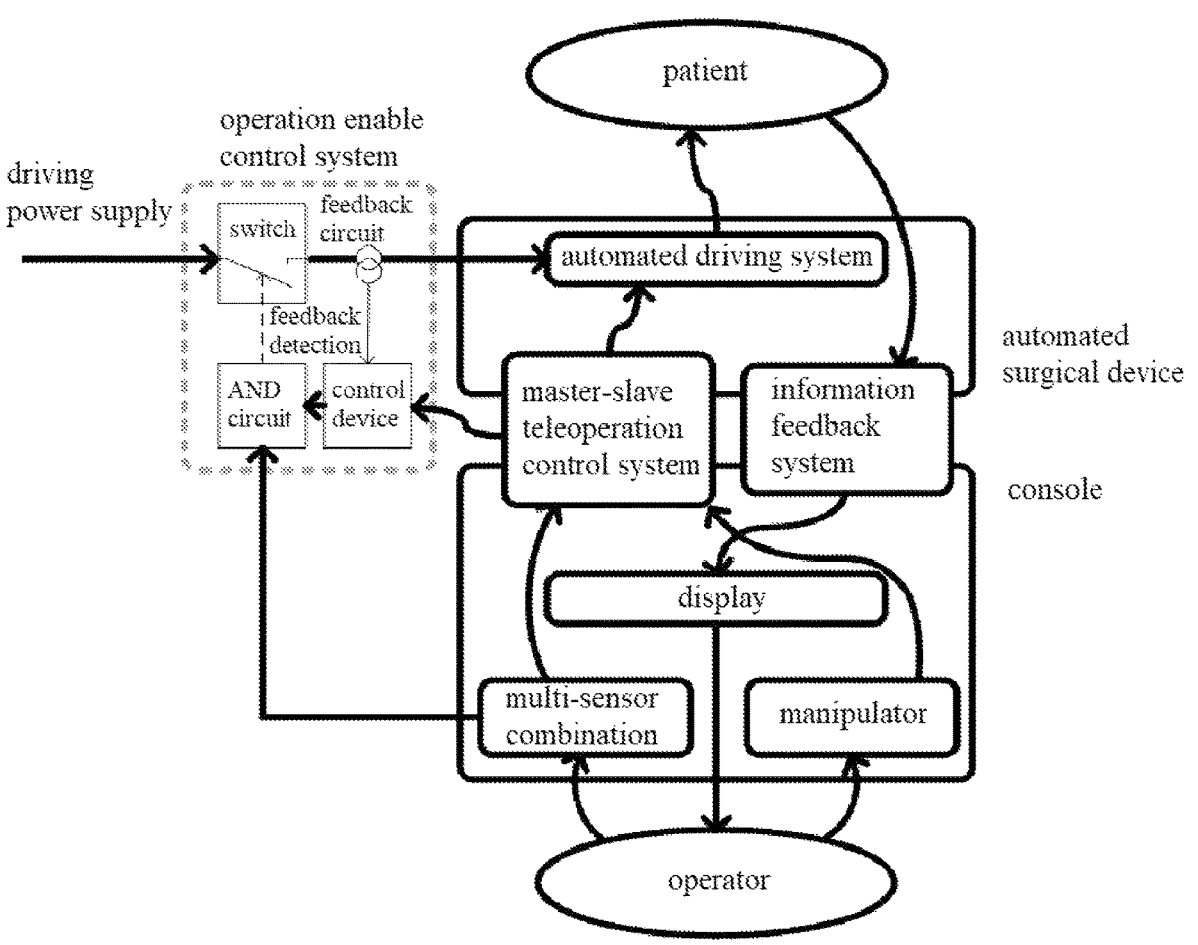
FIG. 2 is a schematic diagram of a workflow of a robot-assisted surgical system including an operation enabling control system according to the present disclosure.

As shown in FIG. 2, this embodiment provides an operation enabling control system for managing a driving power supply of automated surgical device. The operation enabling control system of this embodiment can change the driving power supply from an original direct power supply to controlled power supply. The operation enabling control system provided in this embodiment includes a logical AND circuit, a control device, and a switch element.

The logic AND circuit includes a first input terminal and a second input terminal. The first input terminal of the logic AND circuit can be connected with all sensors in the multi-sensor combination system on a console of a robot-assisted surgical system through an electrical connector, and used to collect operating statuses of all sensors in the multi-sensor combination system. The control device includes an input terminal and an output terminal. The input terminal of the control device is connected with a master-slave teleoperation control system of the robot-assisted surgical system to receive instruction information from the master-slave teleoperation control system. The second input terminal of the logic AND circuit is connected with an output terminal of the control device to receive control signal sent by the control device. The output terminal of the logic AND circuit is connected with a control terminal of a switch element. The logic AND circuit performs a logic AND operation on signals received by the first input terminal and the second input terminal, and a result of the operation is output to control on or off of the switch element. One end of the switch element (a front terminal shown in FIG. 2) is connected with an external power supply system, and another end of the switch element (a back terminal shown in FIG. 2) is connected with a power supply module of an automated driving system. The switch element is connected with a driving power supply loop of an automated surgical device, and turn on or off the driving power supply.

A feedback circuit may also be provided between the switch element and the control device to detect whether there is a supply voltage at the back terminal of the switch element. The feedback circuit is a level detection circuit. For example, an photo coupler or a voltage comparator can perform detection feedback, which can be found in the prior art and will not be described in detail here.

In summary, the operation enabling control system of this embodiment is provided with a control device independent of the master-slave teleoperation control system. The control device can detect a status of a driving power supply through a feedback signal, thereby ensuring reliability of an action of the switch element. When the master-slave teleoperation control system informs the control device that the driving power supply should be off, but the control device detects that the driving power supply is still on, the control device sends a signal to notify the master-slave teleoperation control system that the operation enabling control system has a failure, and the automated driving system is powered. There is a potential risk, and the operation cannot continue. Similarly, when the master-slave teleoperation control system informs the control device that the driving power supply should be on, but the control device detects that the driving power supply is not available, it can also issue a corresponding warning. When other systems of the robot-assisted surgical system detect that a system has a failure and the failure may cause a risk of injury, the control device can be used to quickly and forcibly turn off the driving power supply to ensure personnel safety.

Embodiment 2

Figure 3:
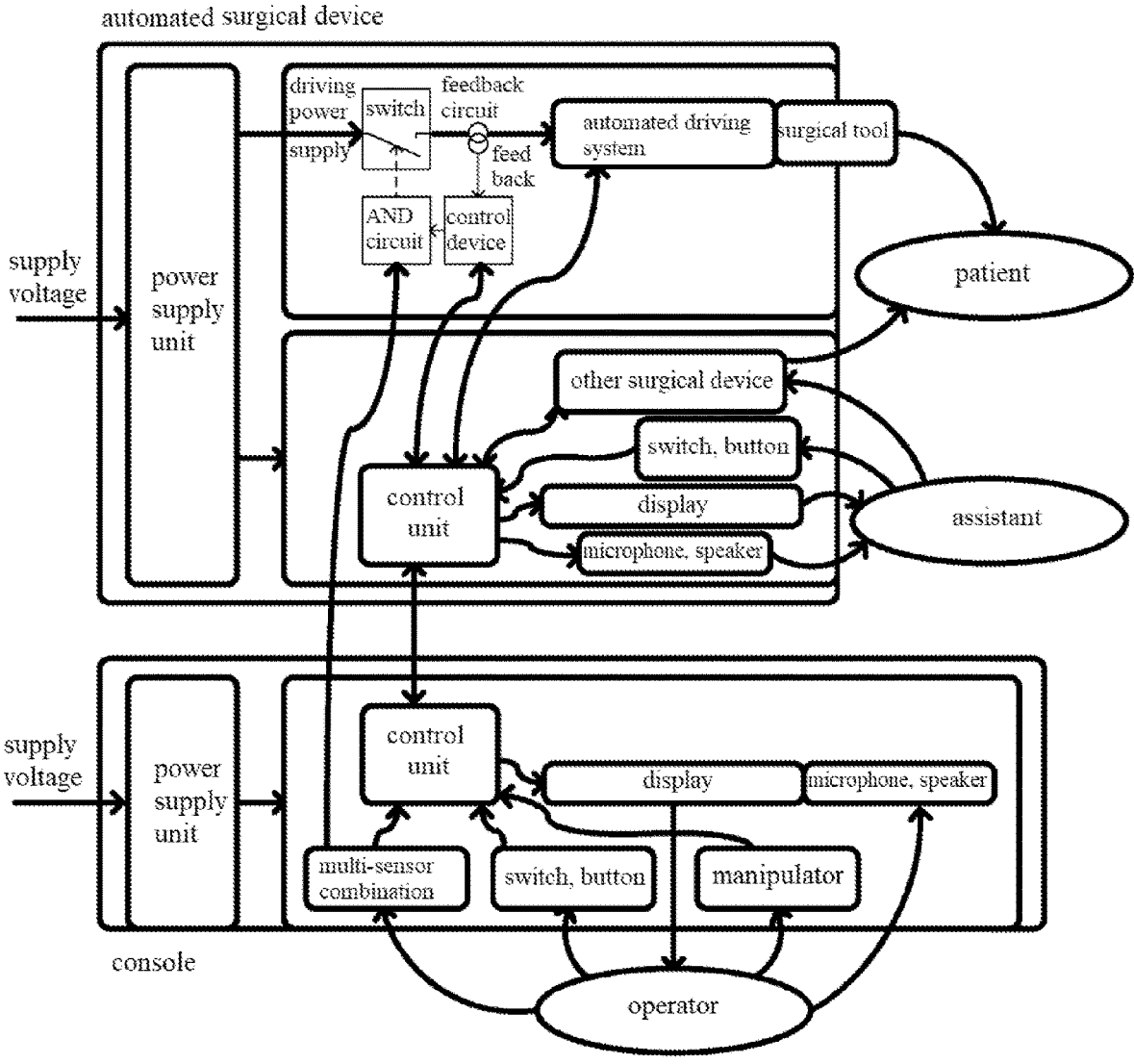
FIG. 3 is a schematic diagram of a structure of a robot-assisted surgical system including an operation enabling control system according to the present disclosure.

As shown in FIG. 3, the present disclosure also provides a robot-assisted surgical device with the operation enabling control system of Embodiment 1, including a console and an automated surgical device. The console includes a console power supply unit, multi-sensor combination system, a switch, a button, a manipulator, a console control unit, a display, a microphone, and a speaker.

Automated surgical device includes surgical device power supply unit, surgical control unit, a switch, a button, a display, a microphone, a speaker, other surgical device (such as high-frequency electrotome, etc.), operation enabling control system, automated driving system, and corresponding surgical tool.

The console power supply unit is connected with an external power supply, converts AC power into working voltage required by various components of the console, and supply power to various components of the console. The multi-sensor combination system is used to detect whether an operator is ready to operate (such as detecting whether a hand or a foot is in a specified position, whether eyes are facing the screen, etc., which can be set according to actual situation, and will not be described in detail here). Input terminals of the console control unit are connected with sensors of the multi-sensor combination system, the switch, the button, the manipulator and the microphone, respectively. Output terminals of the console control unit are connected with the display and speaker. The operator interacts with the console through the devices above.

The surgical control unit is bidirectionally connected with the console control unit, a control device of the operation enabling control system, the automated driving system and other surgical device to perform interactive communication. The surgical control unit controls corresponding electrical driven motion through the automated driving system to drive surgical tool to move. Input terminals of the surgical control unit are connected with the switch, the button and the microphone, respectively. Output terminals of the surgical control unit are connected with the display and the speaker to assist the operator to interact with the automated driving system through the devices above.

The surgical power supply unit is connected with the external power supply network, and converts AC power into working voltage required by various parts of the automated surgical device to supply power to electrical components of the automated surgical device. An operation enabling control system is set between the surgical power supply unit and the automated driving system. A first input terminal of the logic AND circuit of the operation enabling control system is connected with the multi-sensor combination system n parallel. The operation enabling control system can change the surgical power supply unit from an original direct power supply to conrolled power supply. The surgical control unit controls the switch element through a control device of the operation enabling control system.

In summary, when the operator is ready to operate (that is, the operator riggers all detection sensors in the multi-sensor combination system). In an aspect, the surgical control unit detects that all sensors are triggered, and informs the automated driving system to enter movement enabled mode through a software control loop and be ready to start electrical driving operation. And the surgical control unit notifies the control device of the operation enabling control system to output an effective control signal to the logic AND circuit. The control signal and hardware output signals of all sensors in the multi-sensor combination system are collected by the operation enabling control system and used to perform a hardware logical AND operation. An output signal of the logical AND operation is directly used to control on and off of the switch element of the operation enabling control system. Only when all sensors are triggered, the driving power supply of the automated driving system can be supplied, thereby ensuring that the automated surgical device does not take any unexpected action when the operator is not ready to operate. During operation, if any sensor is not triggered (for example, the operator gives up triggering a detection sensor in the multi-sensor combination system), the power supply of the automated driving system can be immediately turn off, so that all electrical driven motion can be stopped quickly. When the operator discovers a dangerous situation, it is obviously faster to stop the automated surgical device by disconnecting any sensor than by press a stop switch. Thus, a risk can be reduced or even avoided.

EXAMPLE 3

Figure 4:
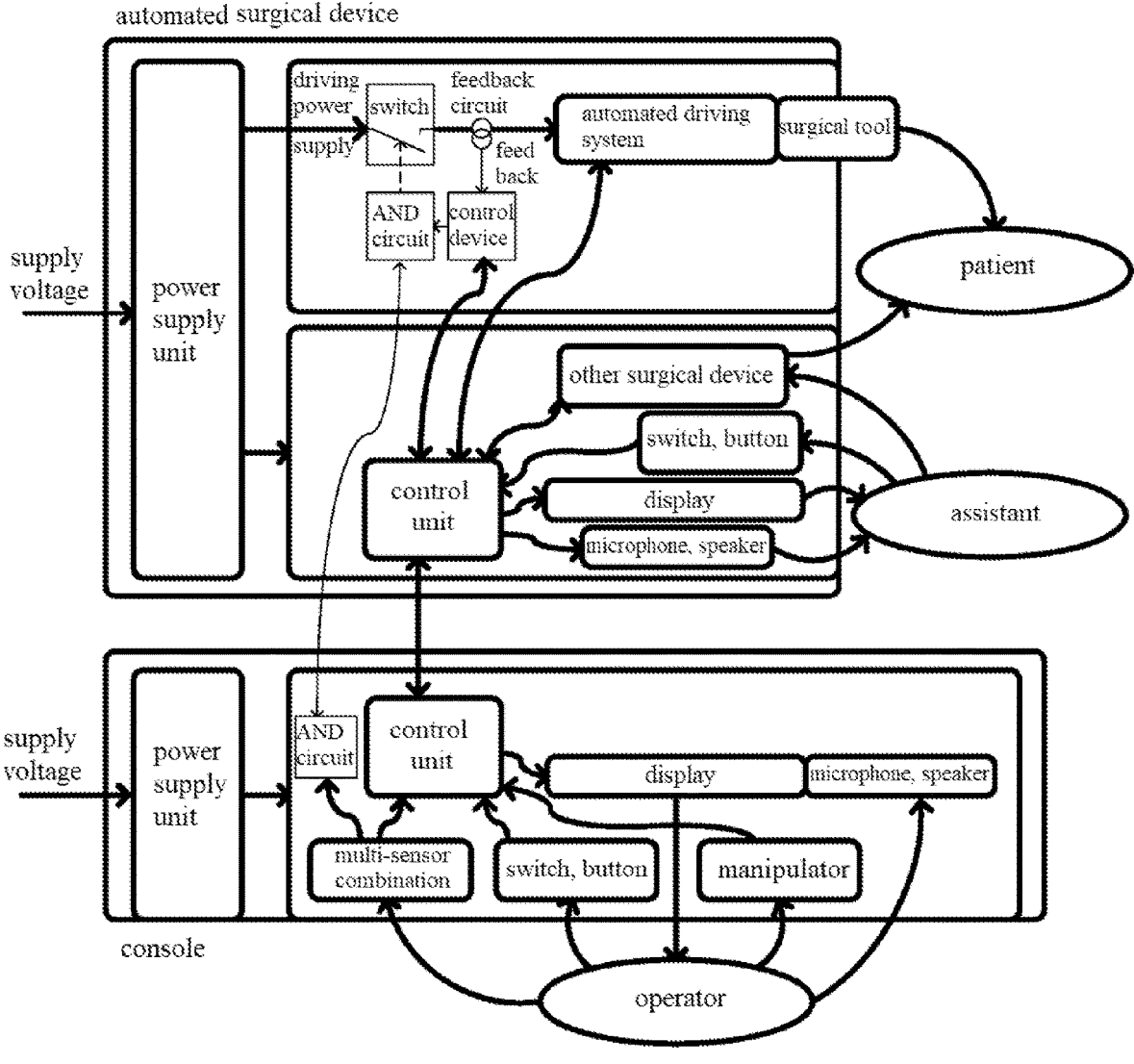
FIG. 4 is another embodiment of a robot-assisted surgical system including an operation enabling control system according to the present disclosure.

As shown in FIG. 4, this embodiment also provides a robot-assisted surgical device with the above-mentioned operation enabling control system, including a console and an automated surgical device. The structures of the console and the automated surgical device is basically the same as that of the embodiment 2. The difference is that the console of this embodiment can also include a logical AND circuit. Input terminal of the logic AND circuit on the console are connected with multi-sensor combination system in parallel. Output terminal of the logical AND circuit is connected with the logic AND circuit of the operation enabling control system in the automated surgical device. The logic AND circuit of the console performs a logical AND operation on the hardware output signals of the multi-sensor combination system. The result of the operation is transmitted to the logical AND circuit of the automated surgical device. A logical AND operation is performed on the result and output signal of the control device in the operation enabling control system, and the operation result is used to control the switch element. An advantage of this implementation is to simplify connection cable between the console and the automated surgical device. The sensors no longer need to be connected with the automated surgical device, but only output signal of the logical AND operation is transmitted to the logic AND circuit of the operation enabling control system in the automated surgical device.

Based on the disclosure and teaching of the foregoing description, those skilled in the related art can also make appropriate changes and modifications to the foregoing embodiments. Therefore, the present disclosure is not limited to the specific embodiments disclosed and described above, and some modifications and changes to the present disclosure should also fall within the protection scope of the claims of the present disclosure. In addition, although some specific terms are used in this disclosure, these terms are only for convenience of description and do not constitute any limitation to the present disclosure.

The invention claimed is:

1. A robot-assisted surgical device, comprising:
a console, wherein the console comprises a sensor system configured to detect whether an operator is ready for conducting an operation; and
an automated surgical device, comprising:
a surgical device power supply unit;
a surgical control unit;
an operation enabling control system; and
an automated driving system,
wherein:
the operation enabling control system is arranged between the surgical device power supply unit and the automated driving system;
the operation enabling control system comprises a control device, a switch element and a logical AND circuit;
the switch element comprises a first terminal connected with the surgical device power supply unit;
the switch element comprises a second terminal connected with the automated driving system;
the control device comprises an input terminal connected with the surgical control unit to receive an operation instruction that corresponds to an operation by an operator, and the control device is configured to generate a control signal based on the operation instruction;
the control device comprises an output terminal configured to output the control signal;
the logic AND circuit comprises a first input terminal configured to receive a sensor status from the sensor system, wherein the sensor status is used to indicate whether the operator is ready to operate;

the logic AND circuit comprises a second input terminal connected with the output terminal of the control device to receive the control signal; and
the logic AND circuit comprises an output terminal connected with a control terminal of the switch element.

2. The robot-assisted surgery device according to claim 1, wherein the first input terminal of the logical AND circuit is connected with one or more sensors of the sensor system.

3. The robot-assisted surgery device according to claim 1, wherein the console further comprises a second logical AND circuit comprising:
an input terminal connected with one or more sensors of the sensor system; and
an output terminal connected with the first input terminal of the logic AND circuit.

4. The robot-assisted surgical device according to claim 1, further comprising:
a feedback circuit connected between the switch element and the control device, the feedback circuit being configured to detect whether the switch element provides a supply voltage to the automated driving system.

5. The robot-assisted surgical device according to claim 1, wherein the console further comprises:
a console power supply unit, a switch, a button, a manipulator, a console control unit, a display, a microphone, and a speaker,
wherein:
the console power supply unit is connected with an external power supply network;
the console control unit comprises input terminals connected with one or more sensors of the sensor system; and
the switch, the button, the manipulator, the microphone, and an output terminal of the console control unit are respectively connected with the corresponding display and speaker to assist the operator to interact with the console.

6. The robot-assisted surgical device according to claim 5, wherein the automated surgical device further comprises:
a switch, a button, a display, a microphone, a speaker, and a corresponding surgical tool,
wherein:
the surgical control unit is connected bidirectionally with the console control unit, the control device, and the automated driving system to perform interactive communication;
the surgical control unit is configured to control a corresponding electrical driven motion through the automated driving system to drive the corresponding surgical tool to move;
the surgical control unit comprises input terminals connected with the corresponding switch, button, and microphone of the automated surgical device; and
the surgical control unit comprises an output terminal connected with the corresponding display and speaker of the automated surgical device to assist the operator to interact with the automated driving system.

7. An operation enabling control system, comprising:
a control device comprising an input terminal and an output terminal;
a switch element comprising a control terminal, a first terminal, and a second terminal; and
a logic AND circuit comprising a first input terminal, a second input terminal, and an output terminal;

wherein:

the first terminal of the switch element is connected with a power supply;

the second terminal of the switch element is connected with an automated driving system of a robot-assisted surgical system;

the input terminal of the control device is connected with the robot-assisted surgical system to receive an operation instruction that corresponds to an operation by an operator, and the control device is configured to generate a control signal based on the operation instruction;

the first input terminal of the logic AND circuit is configured to receive a sensor status of the robot-assisted surgical system, wherein the sensor status is used to indicate whether the operator is ready to operate;

the second input terminal of the logic AND circuit is connected with the output terminal of the control device to receive the control signal; and the output terminal of the logic AND circuit is connected with the control terminal of the switch element.

8. The operation enabling control system according to claim 7, further comprising:

a feedback circuit connected between the switch element and the control device, the feedback circuit being configured to detect whether the switch element provides a supply voltage to the automated driving system.

9. The operation enabling control system according to claim 8, wherein the feedback circuit comprises a level detection circuit.

* * * * *